United States Patent [19]

Eaton

[11] Patent Number: 4,769,020
[45] Date of Patent: Sep. 6, 1988

[54] MALE INCONTINENCE DEVICE AND APPLIANCE AND METHOD OF APPLICATION

[75] Inventor: Ann Eaton, London, England

[73] Assignee: E. R. Squibb & Sons, Inc., Princeton, N.J.

[21] Appl. No.: 948,191

[22] Filed: Dec. 31, 1986

[30] Foreign Application Priority Data

Jan. 21, 1986 [GB] United Kingdom ............... 86-01424

[51] Int. Cl.⁴ ................................................ A61F 5/44
[52] U.S. Cl. .................................................... 604/352
[58] Field of Search ............................. 604/349–353; 128/132 R; 242/DIG. 2

[56] References Cited

U.S. PATENT DOCUMENTS

| 3,364,932 | 1/1968 | Beach ................... | 128/295 |
|---|---|---|---|
| 3,369,546 | 2/1968 | Hickok .................. | 128/295 |
| 3,403,682 | 10/1968 | McDonell ............... | 128/295 |
| 3,421,507 | 1/1969 | Gresham ................ | 604/349 |
| 3,788,324 | 1/1974 | Lim ...................... | 128/295 |
| 3,835,857 | 9/1974 | Rogers et al. .......... | 128/295 |
| 3,863,638 | 2/1975 | Rogers, III et al. ..... | 128/295 |
| 3,916,902 | 11/1975 | Lineberger ............. | 128/295 |
| 4,187,851 | 2/1980 | Hauser .................. | 604/352 |
| 4,378,018 | 3/1983 | Alexander et al. ...... | 128/295 |
| 4,475,909 | 10/1984 | Eisenberg .............. | 604/349 |
| 4,475,910 | 10/1984 | Conway et al. ......... | 604/352 |
| 4,534,768 | 8/1985 | Osburn et al. ......... | 604/350 |
| 4,540,409 | 9/1985 | Nystrom et al. ........ | 604/349 |
| 4,581,026 | 4/1986 | Schneider .............. | 604/352 |
| 4,586,974 | 5/1986 | Nystrom et al. ........ | 156/165 |
| 4,589,874 | 5/1986 | Riedel et al. .......... | 604/349 |
| 4,655,755 | 4/1987 | Ruffini ................. | 604/352 |

FOREIGN PATENT DOCUMENTS

| 1184818 | 4/1985 | Canada . |
|---|---|---|
| 2092690 | 8/1982 | United Kingdom . |
| 2096901 | 10/1982 | United Kingdom . |
| 2120102 | 11/1983 | United Kingdom . |
| 2,125,294 | 3/1984 | United Kingdom . |
| 2126483 | 3/1984 | United Kingdom . |

Primary Examiner—C. Fred Rosenbaum
Assistant Examiner—J. L. Kruter
Attorney, Agent, or Firm—Lawrence S. Levinson; Stephen B. Davis

[57] ABSTRACT

A male incontinence device is in the form of a condom having a urine outlet at its lower end. A self-adhesive strip is made in one piece with, or is attached to, the condom in such a manner that the length of the strip is at an angle of over 45° and less than 90° to the central longitudinal axis of the condom. One or both surfaces of the strip may carry adhesive. An applicator is also disclosed, as is a method of applying and securing a male incontinence device.

6 Claims, 2 Drawing Sheets

MALE INCONTINENCE DEVICE AND APPLIANCE AND METHOD OF APPLICATION

BACKGROUND OF THE INVENTION

There have been many attempts to provide a satisfactory incontinence device for wear by male persons. A satisfactory device can be easily applied, is comfortable and unobtrusive, does not leak, remains securely attached to the wearer over a considerable period without discomfort, even though the wearer may be very active, can accomodate sudden surge flows of urine, is hygienic, is easy and cheap to manufacture, and can be removed without any substantial pain or discomfort to the wearer. The prior art is replete with designs which fulfill some of these requirements but are totally inadequate on others.

Hickok in U.S. Pat. No. 3,369,546 disclose a male incontinence device having a thin walled sheath portion communicating with a thicker walled transverse wall provided with an integral sleeve which may be attached to a tubular drain tube.

Beach in U.S. Pat. No. 3,364,932 discloses a male incontinence device having a structure at mouth of the device for maintaining it in place on the penis. The device has a strip of soft foam material coextensive with the circumference of the mouth which under body temperature tends to adhere to the penis. The device has at the exterior of its mouth means adapted to be tightened about the penis.

Lim in U.S. Pat. No. 3,788,324 discloses a male incontinence device whose entire inside length is coated with an adhesive gel foam. The coating further defines a liquid tight seal. In the preferred embodiment, the device is longitudinally split so that the device can accomodate men of different sizes.

Rogers et al. in U.S. Pat. Nos. 3,835,857 and 3,863,638 disclose a male incontinence device. The device is applied by wrapping a liner pad of soft, liquid tight material between the sheath and the penis. Wrapped around the outside of the sheath is an elastic tape which is narrower than the pad.

Conway et al. in U.S. Pat. No. 4,475,910 disclose a male incontinence device which includes a laminated sheath having an inner layer of latex rubber and an outer layer of silicone rubber. Adhesive is stored between the inner and outer layers when the sheath is rolled. As the sheath is unrolled, adhesive is released from the outer layer and adheres to the inner layer. Upon pressing the sheath against the penis, a leakfree bond is created.

Alexander et al. in U.S. Pat. No. 4,378,018 discloses a drainage device composed of a thin resilient external catheter and an adhesive sealant pad for holding the sheath in place. The pad is formed of compressible, deformable, waterresistant, and elastic sealant material and includes a ring portion adapted to seal about the penis and at least one integral strap portion projecting radially from the ring portion. Osburn et al. in U.S. Pat. No. 4,534,768 disclose an improved sealant pad for sealing and retaining in place the elastic sheath of male urinary drainage catheter.

Riedel et al. in U.S. Pat. No. 4,589,874 disclose an external male urinary drainage catheter combined with a collar for facilitating proper fitting of the catheter upon a patient. The catheter includes a cylindrical section rolled to form a torus that is supported by the collar prior to catheter application.

Schneider in U.S. Pat. No. 4,581,026 discloses an external male catheter also including an adhesive attachment for holding the catheter in place.

Nystrom et al. in U.S. Pat. Nos. 4,540,409 and 4,586,974 disclose an external male urinary drainage catheter combined with a tubular applicator for applying and adhesively securing the catheter to a user.

Flam in United Kingdom Patent Application No. 2,096,901 and Eisenberg in U.S. Pat. No. 4,475,909 disclose a liner for mounting an external catheter sheath on a penis.

Lineberger in U.S. Pat. No. 3,916,902 discloses a male incontinence device that is held in place by fluid under pressure.

Ivans et al. in United Kingdom Patent Application No. 2,126,483 discloses a penial urine ducting device comprising a tubular member having a smooth or smoothly contoured external seating surface and an enlarged, flanged inlet end. In use of the device, the penis foreskin is positioned over the flanged inlet end and against the external seating surface and is then clamped against the seating surface by means of a detachable securing band.

Steer in United Kingdom Patent Application No. 2,125,294 discloses a combined applicator and funnel for a male incontinence device. The applicator is generally cup-shaped and is constructed to make an interengagement with the funnel in such a way as to trap the open end of a condom therebetween. A rubber or like ring is applied to hold the condom in position.

Floyd in United Kingdom Patent Application No. 2,120,102 discloses a method and device for applying an elastic sheath to a penis.

Cochrane in Canadian Patent No. 1,184,818 discloses a male incontinence device comprising a condom-like sheath, an applicator, and a retainer ring.

SUMMARY OF THE INVENTION

This invention relates to a male incontinence device and appliance and method of applying same.

According to one aspect of the invention, there is provided a male incontinence device in the form of a condom having a urine outlet at its lower end, in which a self-adhesive strip is made in one piece with or attached to the condom in such a manner that the length of the strip is at an angle of over 45° and less than 90° to the central longitudinal axis of the condom.

According to another aspect of the invention, there is provided a male incontinence appliance consisting of a device as defined in the preceding paragraph in combination with an applicator which comprises a hollow tubular member open at both ends and having a slot in one wall extending substantially longitudinally.

According to a further aspect of the invention, a method of applying and securing a male incontinence device includes the steps of unrolling the free end of an incontinence condom from a hollow tubular applicator, and wrapping around the shaft of the penis a self-adhesive strip which is made in one piece with, or attached to, the condom at an angle thereto.

The provision of a self-adhesive attachment strip located at an angle, e.g., 60° to 87°, to the condom axis is beneficial in that this strip can be wrapped around the upper portion of the condom and the shaft of the penis therein in such a way that it sticks to itself and provides a very secure yet comfortable attachment of the condom to the penis. The use of the described applicator is advantageous in that it allows the condom to be conveniently carried in rolled-up form and at the same time with a length of the self-adhesive strip handy and properly located ready to be wrapped around the penis. The task of applying a male incontinence device normally being a two-handed task, the provision of the strip in one piece with the condom avoids any problems of loss or misplacing or non-availability of suitable adhesive tape, and also means that the condom cannot become detached from the strip except by a rupture of the material of the strip or the condom.

BRIEF DESCRIPTION OF THE DRAWINGS

The invention will be better understood from the following non-limiting description of an example thereof given with reference to the accompanying drawings in which.

DETAILED DESCRIPTION OF THE INVENTION

Figure 1:
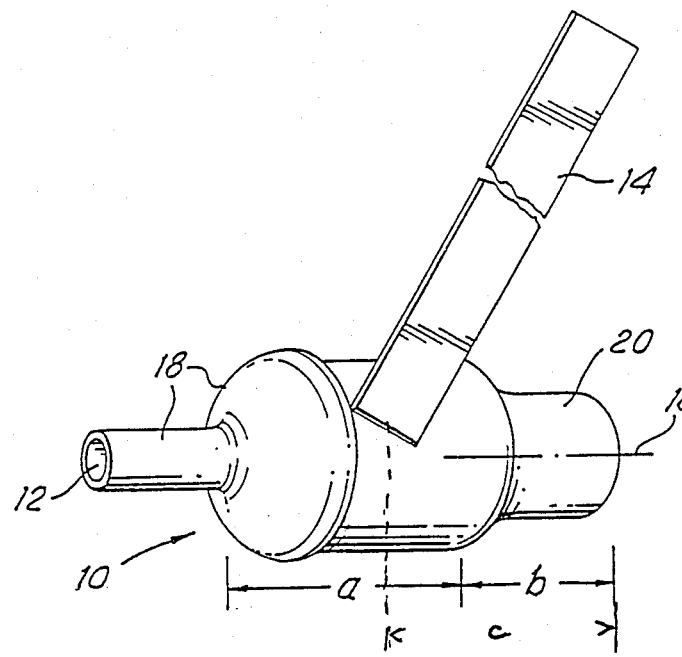
FIG. 1 is a diagrammatic view of one example of male incontinence device according to the invention.

Referring firstly to FIG. 1, the illustrated male incontinence device is in the form of a condom 10 having a urine outlet 12 at its lower end. A self-adhesive strip 14 is made in one piece with or attached to the condom 10 in such a manner that the length of the strip 14 is at an angle of about 78° to the central longitudinal axis 16 of the condom. As will be understood, a drainage tube or pipe of conventional design will in use be attached to the outlet 12. Any desired form of attachment may be used. For example, one could utilize a tube coupling such as described in British Patent No. 2,092,690. The strip 14 should be at an angle between 45° and 90° to the axis 16 and this angle may have a value of over about 60° and less than 87°. A preferred value for this angle would be in the range 70°–85°. The condom is preferably thickened at its lower end as indicated at 18, for example by multiple latex dipping of this portion or by securing a conventional condom to a molded outlet cup. The condom preferred in this invention and illustrated departs from the conventional condom in that it has no bead at its upper, wider end and that, while tubular in shape, this upper end has a diameter of less than the diameter of the condom at its lower end. The reduced diameter upper end 20 may, for example, have a diameter of about two thirds of the condom maximum diameter. The purpose of this reduced diameter portion is to cause the condom to grip firmly behind the head of the penis. The diameter of the reduced diameter portion of the condom can be from about 50% to about 80% of the maximum diameter portion. The length of the relevant portions of the condom may for example be as indicated, the dimension a may be about 1½ inches (about 38 m.m.) and the dimension b may be about 1 inch (25 m.m.). The dimension c may be about 1¾ inches (44 m.m.).

The strip 14 is a self-adhesive strip of stretchable and flexible but substantially waterproof material. For example the strip may be of latex, and it may have a width of from about 10 to about 30 millimeters. The stretchable and flexible strip need not be of latex; one suitable strip is of non-woven fabric impregnated with a plastics such as polyurethane and coated with a nonirritating medical grade adhesive. Suitable medical grade adhesives are disclosed by Chen in U. S. Pat. No. 3,339,546 and Doyle et al. in U.S. Pat. No. 4,551,490. Other medical grade adhesives may be suitable. Normally the adhesive is on the inner surface only but it may be on both strip surfaces. The adhesive coated surface or surfaces of the strip are provided with a silicone paper or other protective cover which can be stripped away when the device is to be applied to the penis.

Figure 2:
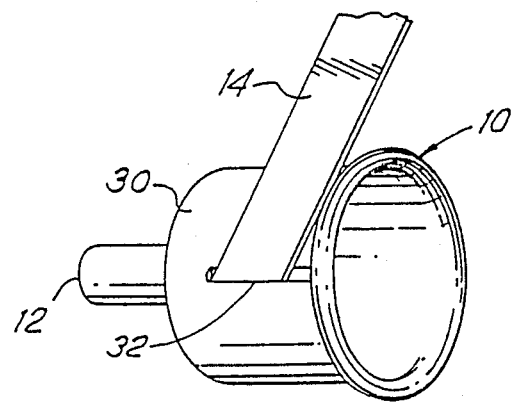
FIG. 2 is a diagrammatic view of the male incontinence device of FIG. 1 located within an applicator with the self-adhesive strip extending from a slot thereof and ready for application to the wearer.
Figure 3:
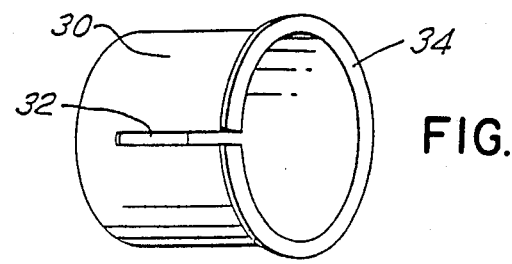
FIG. 3 is a perspective view of one form of applicator forming part of an appliance according to this invention, and for use in a method according to this invention.
Figure 4:
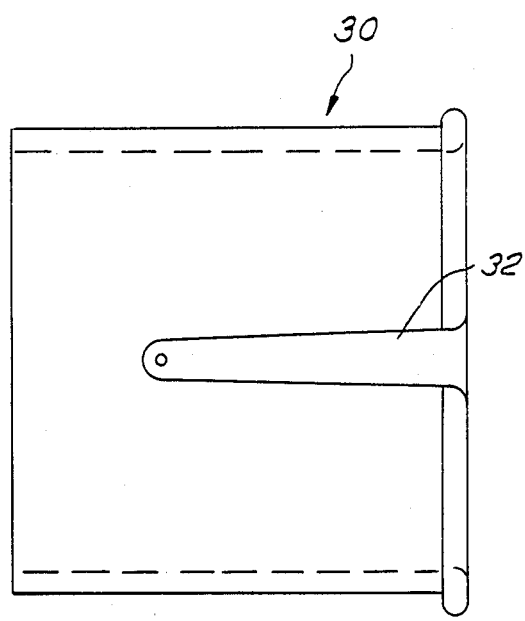
FIG. 4 is an elevation view of the applicator.

One form of applicator is illustrated in FIG. 3 and is formed by a hollow tubular member 30 open at both ends and having a slot 32 in one wall extending substantially longitudinally, that is to say, parallel to the longitudinal axis of the tube. The slot 32 extends to the right hand end as shown in FIG. 3 and that same end is provided with an outwardly extending rim or flange. This is seen at 34 and its purpose is to allow for retention of a rolled up end of a condom securely on the applicator, as best seen in FIG. 2. The rim may be a rounded peripheral bead as seen in FIG. 4.

The manner of application of the condom to the penis of a wearer can be readily understood from a consideration of FIGS. 2 and 3. One starts with the configuration illustrated in FIG. 2 in which the condom outlet end 12 extends out of the left hand end of the applicator member 30 and the selfadhesive strip 14 extends at an angle out of the slot 32. The right hand end of the condom is rolled up over the right hand end of the applicator and is retained on the applicator by the rim 34. When the wearer desires to apply the male incontinence device, the end of the penis is inserted into the applicator, which is of course dimensioned to receive an average sized penis head with a small clearance, and the portion 20 of the condom is unrolled so that it lies along the penis shaft. The applicator is then removed and the strip 14 wound around the outside of the condom up to its end and thereafter around the shaft of the penis. Being self-adhesive, it sticks to itself and securely retains the device on the penis. The strip 14 may be of any suitable length, for example about 10 inches (50 m.m.); for most uses, a length of strip within the range 8–12 inches (200–300 m.m.) is suitable. The strip may be from ½ to one inch (12 to 25 m.m. approx.) in width.

It will be appreciated that modifications can be made without departing from the invention. For example, good results in certain circumstances may be obtained without having the lower (left hand as illustrated) end of the condom of a thickened wall thickness. It may not be necessary in all cases for the condom to have a reduced diameter portion such as 20 seen in FIG. 1. Other variations and alternatives will occur to a man of average skill in the art and such variations and alternatives are considered to be embodied in this invention.

What is claim is:

1. A male incontinence appliance consisting of a male incontinence device comprising a condom having a urine outlet at its lower end and an integral self-adhesive strip attached to the outside surface of the condom in such a manner that the length of the strip is at an angle of over 45° and less than 90° to the central longitudinal axis of the condom and an applicator comprising a hollow tubular member open at both ends and having a longitudinal slot in its wall which starts at one end but does not extend the full length of said applicator and an outwardly extending rim at the sloted end of said tubular member wherein said condom is passed through said hollow tubular member so that said urine outlet extends beyond the tubular applicator, said self-adhesive strip extends through said slot, and the upper free end of said condom is rolled over said rim.

2. The device according to claim 1 in which the strip is at an angle from 70°–85° to the condom central longitudinal axis.

3. The device according to claim 3 in which the lower end of the condom has an increased wall thickness.

4. The device according to claim 1 in which the lower end of the condom has an increased wall thickness.

5. The device according to claim 1 in which the strip is of non-woven fabric impregnated with plastics material and carrying a medical grade adhesive on one surface.

6. A method of applying and securing a male incontinence device which comprises:

(a) assembling a male incontinence appliance consisting of a condom having a urine outlet at its lower end and an integral self-adhesive strip attached to the outside surface of the condom in such a manner that the length of the strip is at an angle of over 45° and less than 90° to the central longitudinal axis of the condom and an applicator comprising a hollow tubular member open at both ends and having a longitudinal slot in its wall which starts at one end but does not extend the full length of said applicator and an outwardly extending rim at the slotted end of said tubular member wherein said condom is passed through said hollow member so that said urine outlet extends beyond the tubular applicator, said self-adhesive strip extends through said slot, and the upper free end of said condom is rolled over said rim;

(b) inserting the penis of the user into the slotted end of said hollow member;

(c) unrolling the free end of said condom along the shaft of the penis;

(d) removing the applicator; and (e) winding the self-adhesive strip around the outside of the condom to securely retain the condom on the penis.

* * * * *